United States Patent

Sugarbaker

[11] Patent Number: 5,766,187
[45] Date of Patent: Jun. 16, 1998

[54] MECHANISM FOR GUIDING SURGICAL INSTRUMENTS

[76] Inventor: David J. Sugarbaker, 1015 Brook Rd., Milton, Mass. 02186

[21] Appl. No.: 540,719

[22] Filed: Oct. 11, 1995

[51] Int. Cl.⁶ ................................................. A61B 17/04
[52] U.S. Cl. ...................... 606/148; 606/222; 606/144; 606/139; 606/191
[58] Field of Search ........................ 606/222, 223, 606/148, 145, 144, 139, 1, 191, 198; 128/772; 604/104

[56] References Cited

U.S. PATENT DOCUMENTS

| | | | |
|---|---|---|---|
| 2,259,488 | 10/1941 | Raiche | 604/104 |
| 3,079,606 | 3/1963 | Bobrov et al. | |
| 3,490,675 | 1/1970 | Green et al. | |
| 3,499,591 | 3/1970 | Green | |
| 4,509,516 | 4/1985 | Richmond | 606/148 |
| 4,545,373 | 10/1985 | Christoudias | 606/148 |
| 4,773,417 | 9/1988 | Moore et al. | |
| 5,040,715 | 8/1991 | Green et al. | |
| 5,234,454 | 8/1993 | Bangs | 606/191 |
| 5,250,053 | 10/1993 | Snyder | |
| 5,281,236 | 1/1994 | Bagnato et al. | |
| 5,417,690 | 5/1995 | Sennett et al. | 606/61 |
| 5,527,298 | 6/1996 | Vance et al. | 606/191 |

FOREIGN PATENT DOCUMENTS 0138089   4/1985   European Pat. Off. ............... 606/191

OTHER PUBLICATIONS

Sabiston, David C., Jr., Atlas of General Surgery, p. 789, W.B. Sauders (Harcourt Brace & Co.) ISBN 0-7216-7883-1 (1994).

*Primary Examiner*—Michael Powell Buiz
*Assistant Examiner*—Tina T. P. Pham
*Attorney, Agent, or Firm*—Hamilton, Brook, Smith & Reynolds, P.C.

[57] ABSTRACT

A mechanism for guiding an instrument to and locating it at a surgical site comprising a flexible, movable, elongated guide having a proximal end constructed to receive a projecting portion of a surgical instrument and a distal end constructed to receive a flexible leader. There is at least one dilating portion located between the proximal and distal ends to dilate an area at the site to which the surgical instrument is being guided before the instrument reaches the site and while the guide is pulled in the direction of the distal end to facilitate locating the instrument in the area without injuring adjacent tissue.

19 Claims, 6 Drawing Sheets

MECHANISM FOR GUIDING SURGICAL INSTRUMENTS

BACKGROUND OF THE INVENTION

This invention relates to surgery and more particularly to surgery in complicated and dangerous areas. In thoracic surgery, many surgical procedures are performed with instruments such as clamps and staplers and the like which operate in extremely delicate and dangerous areas. One such area is the lung that contains arteries and veins that exit the heart in the hilum. Numerous arteries and veins are located in this area in close proximity to one another. Accordingly, many such arteries and veins are in precarious positions relative to a target artery on which the surgeon is performing an operative technique. Likewise, the airways may be objects at dissection. Similar situations occur in the abdominal cavity.

The present invention relates to a device for safely guiding an instrument to and locating it at a surgical site.

The pulmonary artery, for example, directs blood from the ventricle of the heart to the lungs. The artery normally branches into a right and left pulmonary artery supplying, respectively, the right and left lungs. After the first branch, each artery branches again to supply blood to particular locations of each lung. Assuming that a segment of the lung requires resection because it is cancerous, it is first necessary to terminate the arterial supply of blood to just the segment of the lung which is being resected and not the other. This has traditionally been done in open surgery by clamping and tying off that portion of the pulmonary artery after the first branch which directs blood to the diseased lung and then severing it. In many instances this procedure has been replaced by endoscopic surgery wherein techniques are performed internally with instruments passing through apertures formed in the chest. Clamps are passed through the apertures to clamp and tie the vessels and/or staplers have been developed for "tying off" an artery by rows of tiny staples on both sides of a line which is cut by a blade. This ligates the artery to prevent the flow of blood from the artery into the chest cavity and to prevent regurgitation of blood from the lung back into the chest cavity.

It is a general object of this invention to produce a guide or safety device for positioning such instruments such as clamps or a linear stapler at the surgical site to divide blood vessels or the airways. Similar conditions apply in the abdomen.

An object of employing a guiding device is to secure the structure, such as one of the pulmonary arteries, to which the surgeon wishes to apply a clamp or stapler, in a fixed position and preventing the artery from moving. Another purpose of using a positioning guide is that of displacing other structures, such as the ascending aorta or the arch of the aorta, away from the structure to be stapled. It is desirable that the adjacent structure be pushed away from the surgical site which would otherwise interfere with the stapling operation or be ruptured or otherwise injured unintentionally. The third object of using a positioning guide is to create a channel behind the structure (artery) to be operated upon which is then gradually expanded to allow it to reach the required size to accommodate a stapler or other instrument.

The pulmonary artery, for example, is a low-pressure vessel. Therefore, it has a thin wall. If too much stretch is applied to it, the walls will thin down excessively and possibly tear. Furthermore, the staples may be ineffectively applied. Thus, excessive thinning of the arterial wall is to be avoided. It is normally desired that most of the dilation be against supporting tissues and not the primary or target structure. It is acceptable that the channel being formed for the insertion of the clamp be least against the target and the majority against tissues not being operated on.

While the present invention will be described with regard to endosurgery in the thoracic area, it will be understood that it is not so limited and may be employed in surgical procedures in other areas and on other organs or any other structure requiring careful and precise manipulation of a surgical instrument in open or traditional surgery as well as endoscopic surgery.

SUMMARY OF THE INVENTION

The invention resides in a mechanism for guiding a surgical instrument to and locating it in a surgical site. For purposes of illustration, the site is adjacent the right pulmonary artery although the principles of the invention are applicable to any site. The guiding mechanism comprises a flexible, movable, elongated guide having a proximal end and a distal end. The proximal end is constructed to removably receive a projecting portion of a surgical instrument. The illustrated embodiment of the surgical instrument is an in-line surgical stapler. The proximal end may have alternative configurations to attach securing to other instrumentation tips including vascular or other clamps. This may embody different proximal end configurations. The guide has at least one dilating portion which is located between the proximal and distal ends.

To dilate an area at the site to which the surgical instrument is being guided, dilation takes place before the instrument reaches the site and while the guide is being pulled by the distal end. This is done to facilitate locating the instrument in the site without injuring adjacent tissue or elements.

The distal end of the guide is constructed to receive a flexible leader such as silk suture material which is initially inserted at the site and is used to pull the leader into position in the site before the leader itself is grasped. The proximal end of the guide is funnel-shaped, elastomeric and expandable in order to be removably positioned over a projecting portion of the surgical instrument.

The guide is made of a bio-compatible elastomeric plastic such as polyvinyl chloride although many other bio-compatible elastomeric materials are satisfactory.

The dilating portion can assume numerous shapes and configurations. A preferred shape is a tapered, bulbous expansion in the guide which is hollow. In another embodiment, the dilating portion is funnel-shaped and tapering toward the distal end of the guide, i.e. the end to which the leader is attached. The dilating portion or portions are essentially the same diameter as the funnel-shaped attaching member at the proximal end of the guide.

The distal end of the guide is constructed to receive the leader and may assume numerous configurations. For example, it may have a simple aperture, a notched portion at the distal end or a grooved, crimped portion having an aperture to receive the leader which is knotted. In other variations, the leader may be looped. The guide may be constructed to perform the dilation in more than one step by providing two dilators and the leader. The one nearest the distal end preferably would be smaller than the one closer to the proximal end such that dilation is a two or more step procedure. In the latter instance, a third yet smaller dilating portion would be provided on the leader.

Alternately, the dilating portion may be an inflatable balloon positioned along the guide to dilate to a decimal diameter before positioning of the instrument. It can simply be a thinned-wall portion of the hollow guide inflatable by air pressure.

In endoscopic surgery a two-dimensional camera view of the arterial structure is used in the majority of procedures. This two-dimensional view does not give the surgeon the three-dimensional depth perception so critical in many situations. This invention is also a means of providing a special guide to the surgeon that mechanically simulates three-dimensional views in open surgery by guiding instruments to the proper visual depth for completing the surgery. Thus, the invention may be used only as a guide or as an anatomic member during endoscopic surgery.

The above and others features of the invention, including various and novel details of construction and combination of parts, will now be more particularly described with reference to the accompanying drawings and pointed out in the claims. It will be understood that the particular mechanism for guiding surgical instruments embodying the invention is shown by way of illustration only and not as a limitation of the invention. The principles and features of this invention may be employed in varied and numerous embodiments without departing from the scope of the invention.

DETAILED DESCRIPTION OF THE INVENTION

Figure 2:
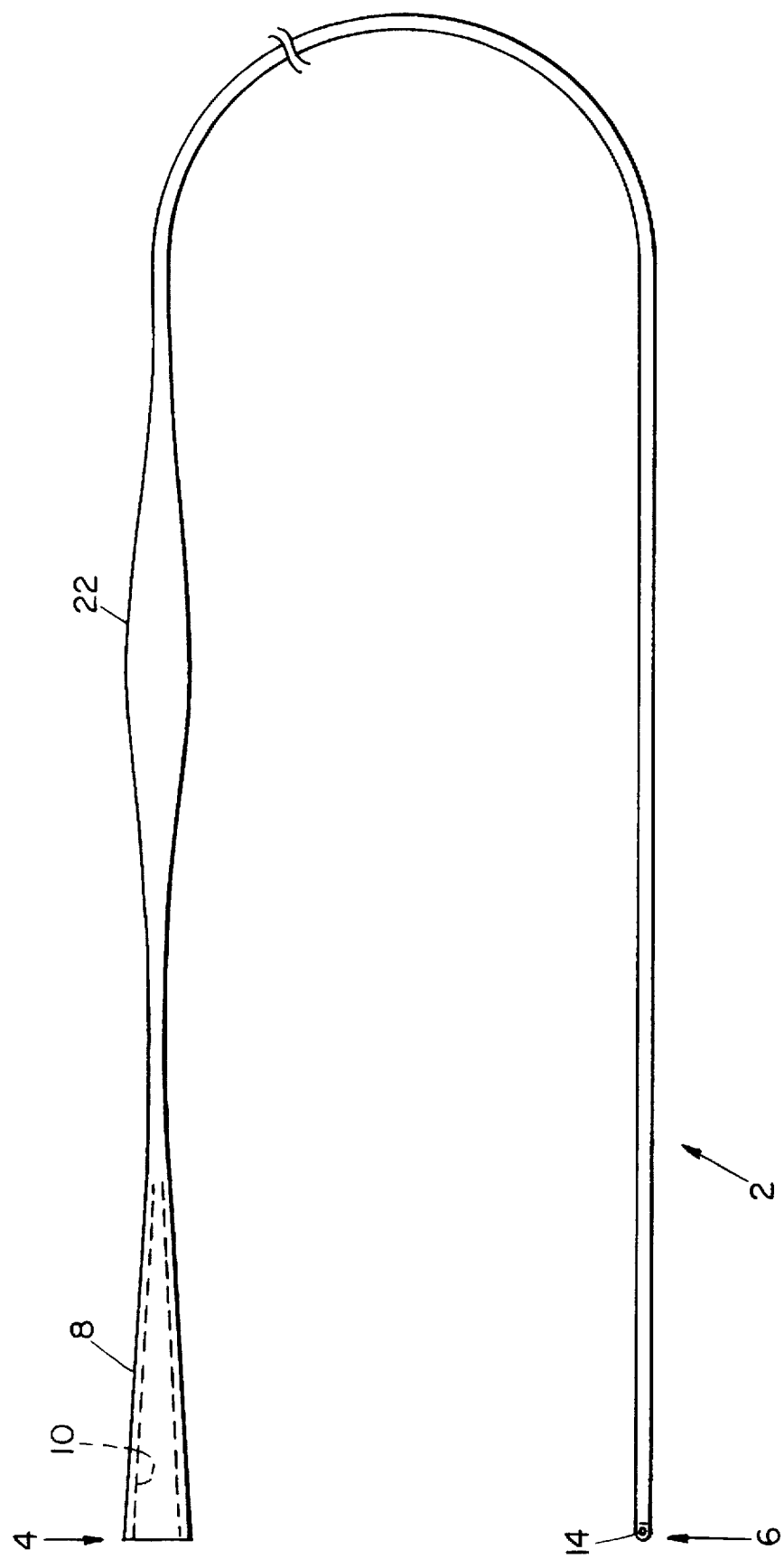
FIG. 2 is a view of said one embodiment of the surgical guide.

One embodiment of my surgical guide 2 will be seen in FIG. 2 and comprises a flexible, movable, elongated member having a proximal end 4 and a distal end 6. The guide is made of a bio-compatible plastic and, for this purpose, polyvinyl chloride has been found to be satisfactory. The proximal end is substantially funnel-shaped, flexible and elastomeric, as seen at 8. As constructed, the entire guide 2 is hollow but need not necessarily be so. The funnel-shaped portion 8 has an open interior designated 10 and while the remainder of the guide may be hollow, it is not illustrated as such for the sake of clarity.

Figures 6, 7, 8:
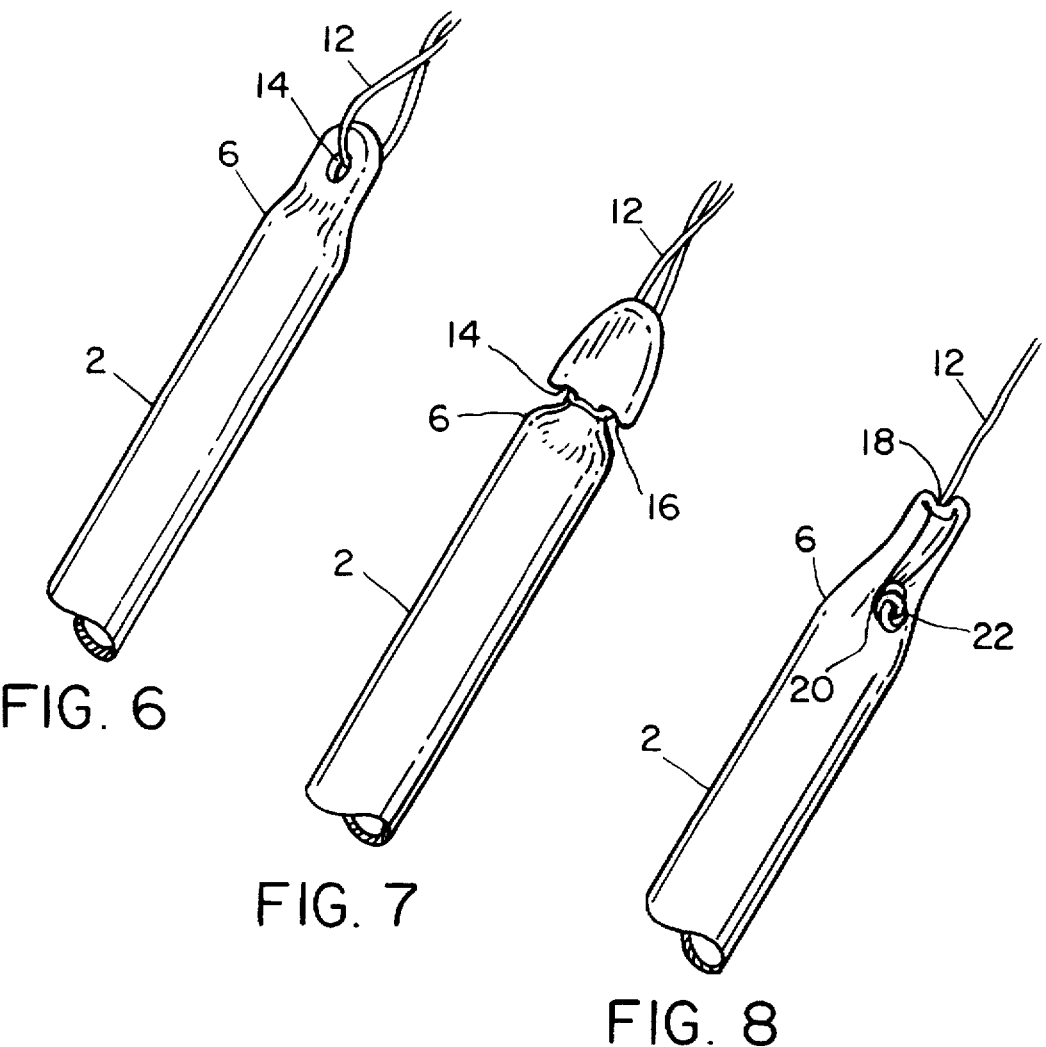
FIGS. 6, 7 and 8 are views of constructions for attaching a leader to the distal end of the surgical guide.

The distal end 6 is constructed to receive a flexible leader 12 such as silk suture material. The distal end may be constructed in various ways to receive a leader 12 as shown in FIGS. 6–8. The leader may be conventional suture material.

In FIG. 6, the distal end 6 of the guide has been flattened under heat and pressure and is provided with an aperture 14 through which the leader 12 passes. As will be seen in FIG. 7, the distal end 6 is notched at 15 and 16. In FIG. 8, the distal portion 6 is formed with a grooved, crimped portion 18 and has an aperture 20 through which the leader 12 passes and is knotted at 22. Other equivalent means for attaching the leader are in the scope of the present invention.

Referring again to FIG. 2, at least one dilating portion of the guide is located between the proximal and distal ends 4 and 6. The dilating portion 22 as seen in FIG. 2 is shaped as a tapered, bulbous expansion in the guide and is essentially the same diameter as the funnel-shaped end 8 at proximal portion 4. The portion 22 dilates an area at the site to which a surgical instrument is being guided (see FIG. 1) before the instrument reaches the site to facilitate locating the instrument in an area by first determining if a channel can be safely developed before positioning the instrument without injuring tissue. The guide may be pulled first by the leader 12 (FIG. 1) and later by the distal end in the direction of the distal end.

Figure 4:
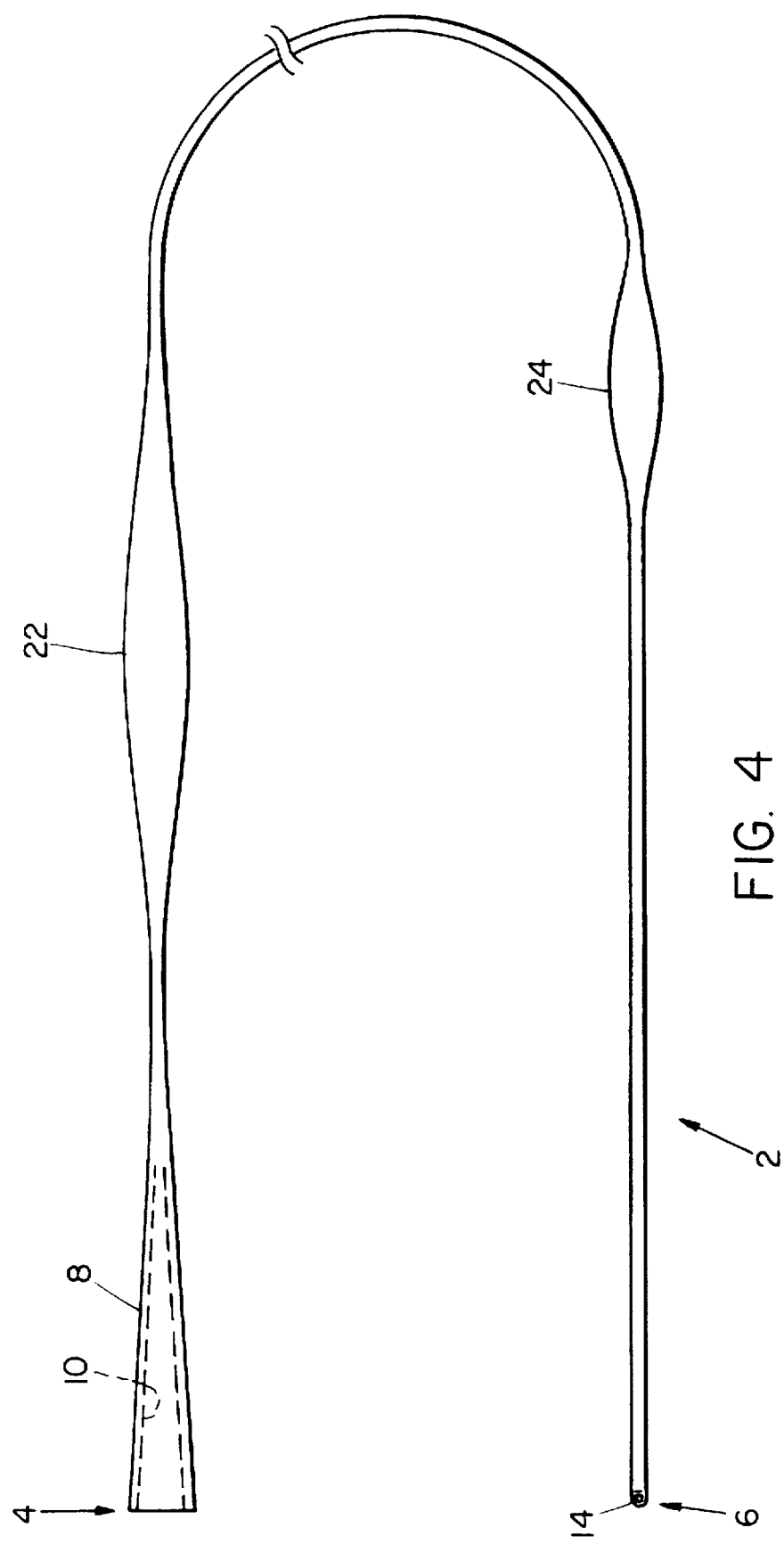
FIG. 4 is a view of another embodiment.

Referring next to FIG. 4, another embodiment of the invention will be seen. It includes, in addition to the dilating portion 22, an additional dilating portion 24 which is also a tapered, bulbous expansion in the guide. However, it is of smaller diameter than the dilating portion 22 such that when the guide is pulled from the distal end, dilating is performed progressively. It is within the scope of this invention to provide additional dilating stations if desired.

Figure 3:
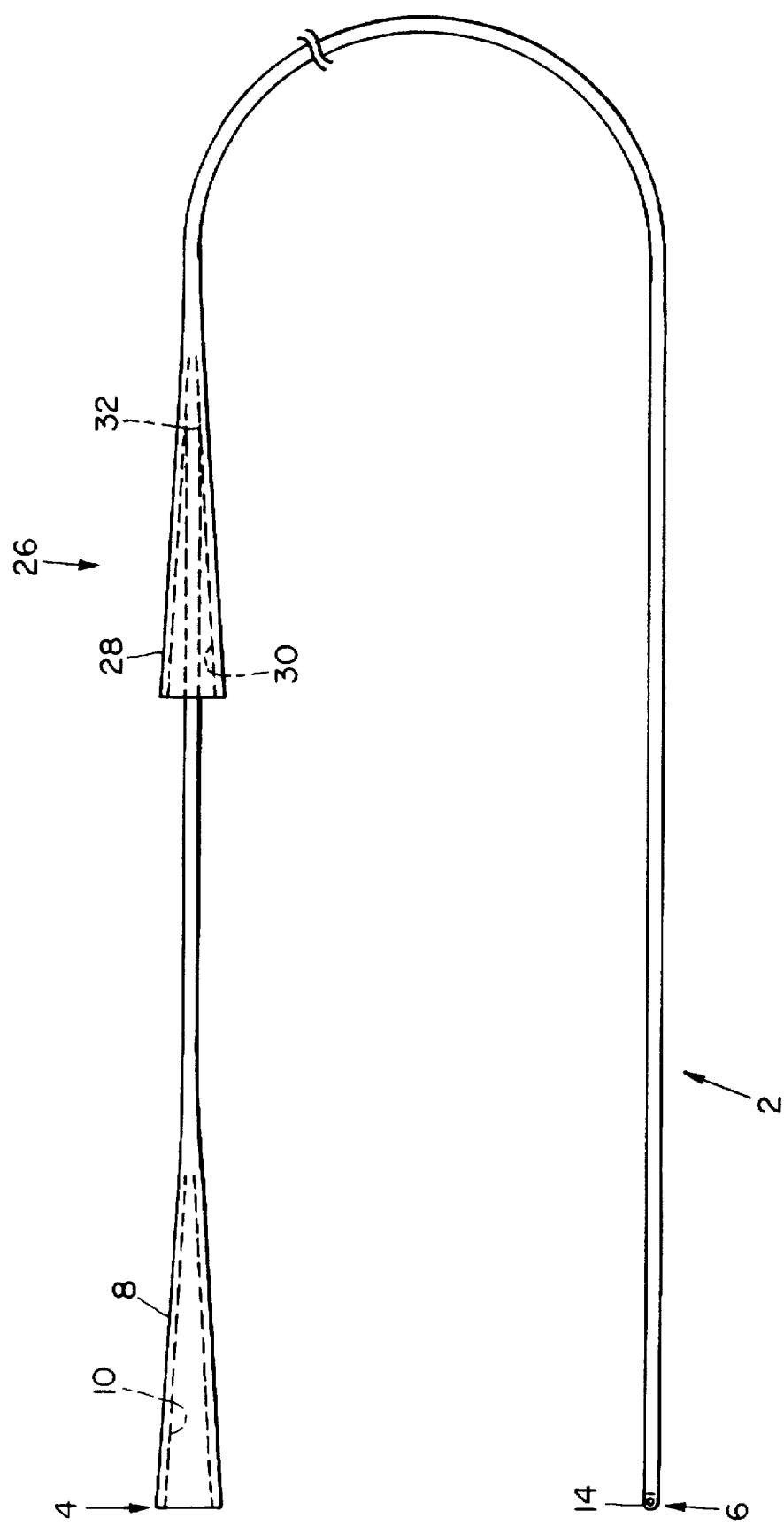
FIG. 3 is a view of another embodiment of the surgical guide.

FIG. 3 shows another embodiment of the invention. In this instance, the dilating portion is essentially the same as the hollow funnel-shaped end 8 at the proximal end 4 of the guide. It, too, is elastomeric and expandable as is the gripping portion 8. It is designated 26 and has a funnel-shaped tapered exterior 28 and a funnel-shaped hollow interior 30. Its diameter is essentially the same as the diameter of the gripping portion 8. It may be constructed by joining two guides together, cutting one guide at a point 32 and forcing it into the interior 30 of the principal guide. It can either be force-fit into the interior or, if desired, secured by an adhesive.

Figure 5:
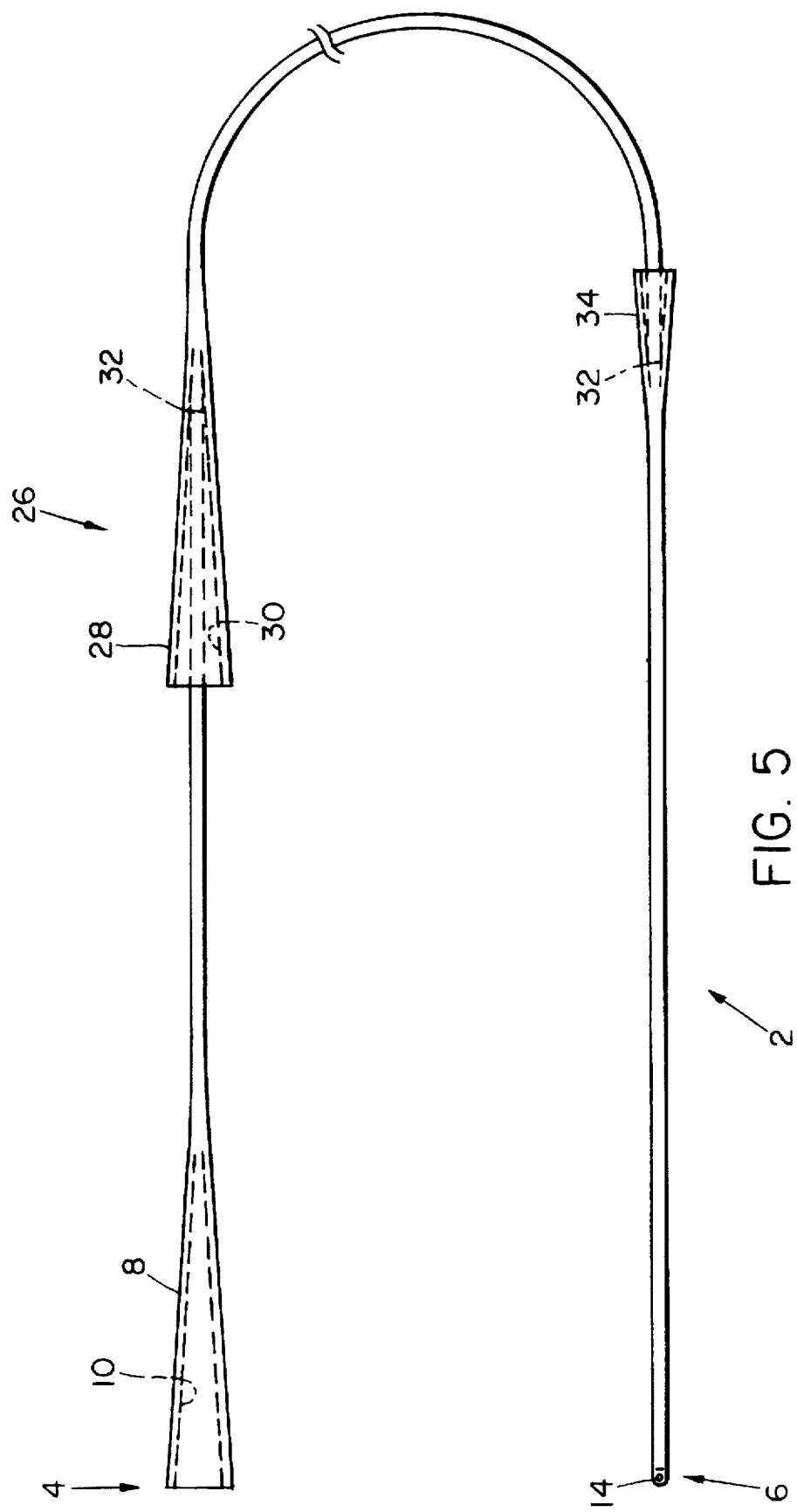
FIG. 5 is a view of yet another embodiment.

FIG. 5 is yet another embodiment of the invention wherein there is an additional leading dilating portion 34 in advance of the funnel-shaped dilator 26. It would be made in a manner similar to the embodiment of FIG. 3 except that its diameter is smaller than the diameter of dilator 26 in order to permit progressive dilation as the leader moves toward the direction of the distal portion 6 as will be described in detail hereinafter.

Figure 1:
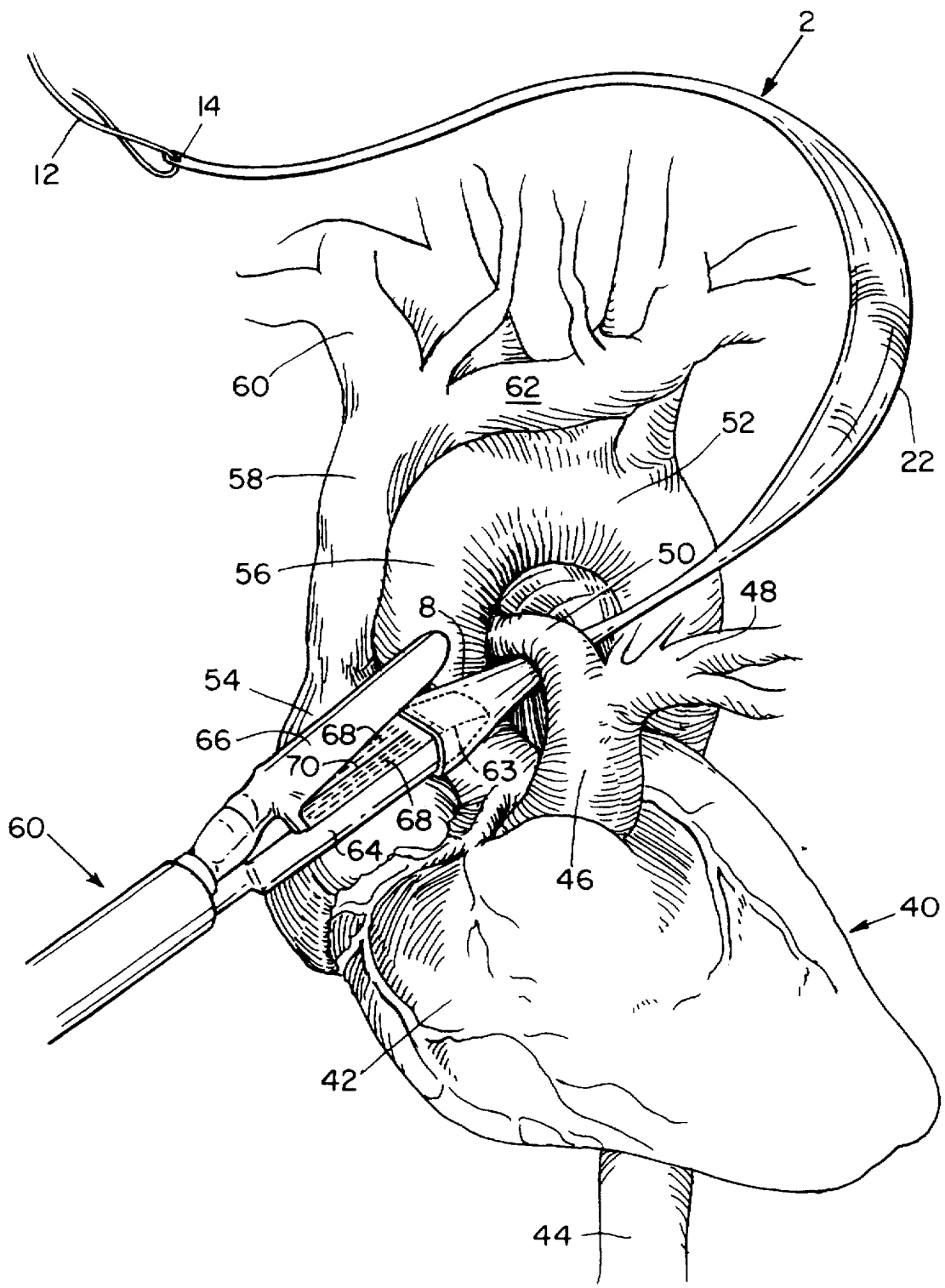
FIG. 1 is a graphic portrayal of a human heart having a stapler being guided to a surgical site adjacent to a portion of the left pulmonary artery by one embodiment of the present invention.

The guide operates in the following manner. FIG. 1 shows a human heart and various appendages with a linear stapler generally indicated 60 being guided by a flexible, elongated guide 2 (the subject matter of the present invention). The heart is generally indicated 40; the right ventricle 42; the thoracic aorta 44; the main pulmonary artery 46; the left branch or the left pulmonary artery 48; the right branch or right pulmonary artery 50; the arch of the aorta 52; the right auricle appendix 54; the ascending aorta 56; the superior vena cava 58; the right vena innominata and the left vena innominata 63.

In the present instance, the surgeon is going to remove a portion of the right lung to which blood flows from the right pulmonary artery 50. The artery must be stapled and severed in order to cut off the flow of blood. Hence, the operative site in this specific instance is the right pulmonary artery. The anvil portion 66 of the stapler 60 is in its open or inoperative position above the cartridge 64. The stapler includes a plurality of recesses 68 in the anvil on both sides of a severing line 70 through which a blade passes to sever the artery after staples have been driven. In this instance three rows of staples will be on each side of the severed artery.

The surgeon or his assistant places the funnel-shaped distal end 8 of the guide 2 over the tip 63 of the cartridge 64 of the stapler, being careful not to obstruct the staple recesses 68. The right pulmonary artery is raised by the surgeon with an angled instrument sufficient to pass the leader 12 under the artery. The leader 12 with the guide attached is then pulled from the distal end to lead the guide 2 under the artery until the dilating portion 22 raises the artery from the surrounding tissues and structures. Continued pulling of the guide locates the anvil of the stapler safely beneath the artery in the area heretofore dilated by the portion 22. The proximal portion 8 of the guide may then be removed from the stapler with the anvil then in place. The driver 66 closed and the stapler fired to staple and sever the artery.

If desired, a guide 2 such as that shown in FIG. 4 may be used where the dilation is accomplished in two stages, first by the smaller bulbous portion 24 which partially dilates, and secondly by the bulbous portion 22 which completes the dilation.

In like manner, the dilators shown in FIGS. 3 and 5 may be used where dilation may take place in either one stage or two stages as desired. The procedure is the same as with the FIG. 2 guide.

The invention claimed is:

1. Mechanism for guiding an instrument to and locating it at a surgical site comprising:

a movable, elongated guide having a proximal end and a distal end;

the guide being flexible from end to end;

the distal end being reduced in size, shaped to receive a flexible leader;

the proximal end being funnel-shaped to be removably positioned over a projecting portion of a surgical instrument; and at least one dilating portion located between the proximal and distal ends to dilate an area at the site to which the surgical instrument is being guided before the instrument reaches the site and while the guide is pulled in the direction of the distal end to facilitate locating the instrument in the area without injuring adjacent tissue.

2. Mechanism in accordance with claim 1, wherein the guide is made of a bio-compatible plastic.

3. Mechanism in accordance with claim 1, wherein the guide is made of polyvinyl chloride.

4. Mechanism in accordance with claim 1, wherein the dilating portion is a tapered, bulbous expansion in the guide.

5. Mechanism in accordance with claim 1, wherein the dilating portion is funnel-shaped and tapers toward the distal end.

6. Mechanism in accordance with claim 1, wherein the distal end having an aperture to receive a leader.

7. Mechanism in accordance with claim 1, wherein the distal end having a notched portion to receive a leader.

8. Mechanism in accordance with claim 1, wherein the distal end having an aperture adjacent a grooved, crimped portion to receive a leader.

9. Mechanism in accordance with claim 1, wherein there is a second dilating portion between the said one dilating portion and the distal end.

10. Mechanism in accordance with claim 4, wherein the bulbous expansion is essentially the same diameter as the funnel-shaped end of the guide.

11. Mechanism for guiding an instrument to and locating it at a surgical site comprising:

a flexible, movable, elongated guide having a proximal end and a distal end;

the distal end being reduced in size, shaped to receive a flexible leader;

the proximal end being funnel-shaped to be removably positioned over a projecting portion of a surgical instrument;

at least one dilating portion located between the proximal and distal ends to dilate an area at the site to which the surgical instrument is being guided before the instrument reaches the site and while the guide is pulled in the direction of the distal end to facilitate locating the instrument in the area without injuring adjacent tissue, and a leader attachable to the distal end to assist in locating the guide at the surgical site.

12. Mechanism in accordance with claim 11, wherein the guide is made of a bio-compatible plastic.

13. Mechanism in accordance with claim 11, wherein the guide is made of polyvinyl chloride.

14. Mechanism in accordance with claim 3 wherein the dilating portion is a tapered, bulbous expansion in the guide.

15. Mechanism in accordance with claim 11, wherein the dilating portion is funnel-shaped and tapers toward the distal end.

16. Mechanism in accordance with claim 11, wherein the distal end having an aperture to receive a leader.

17. Mechanism in accordance with claim 11, wherein the distal end having a notched portion to receive a leader.

18. Mechanism in accordance with claim 11, wherein the distal end having an aperture adjacent a grooved, crimped portion to receive a leader.

19. Mechanism in accordance with claim 11, wherein there is a second dilating portion between the said one dilating portion and the distal end.

* * * * *